(12) United States Patent
Henshilwood et al.

(10) Patent No.: US 6,271,371 B1
(45) Date of Patent: Aug. 7, 2001

(54) OXIDATIVE PROCESS AND PRODUCTS THEREOF

(75) Inventors: James Henshilwood; Nicholas Bernard Johnson, both of Cambridge (GB)

(73) Assignee: Janssen Pharmaceutica, N.V. (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/404,035

(22) Filed: Sep. 23, 1999

Related U.S. Application Data

(63) Continuation of application No. 08/875,638, filed on Jul. 16, 1997.

(30) Foreign Application Priority Data

Apr. 3, 1995 (GB) .................................. 9506843

(51) Int. Cl.[7] ........................ C07D 487/06; C07D 491/06
(52) U.S. Cl. ............................... 540/521; 540/576
(58) Field of Search ..................... 540/521, 576

(56) References Cited

U.S. PATENT DOCUMENTS

| | | | |
|---|---|---|---|
| 4,239,605 | * 12/1980 | Vlahov et al. | 204/59 |
| 4,290,862 | * 9/1981 | Vlahov et al. | 204/59 |
| 6,018,043 | * 1/2000 | Dyer et al. | 540/520 |
| 6,084,094 | * 7/2000 | Henshilwood et al. | 540/543 |

FOREIGN PATENT DOCUMENTS

| | | |
|---|---|---|
| 401058 | 6/1996 | (AT) . |
| 8808708 | 11/1988 | (WO) . |

OTHER PUBLICATIONS

Kametani et al. (J. Chem. Soc. C (1971), 6, 1043–7).*
Szewczyk, J. et al. (1988) "An improved synthesis of galanthamine" J. Heterocyclic Chem. 25(6):1809–1811.
Kametani, T. et al. (1969) "Studies on the Syntheses of Heterocyclic Compounds. Part CCCXV. Modified Total Syntheses of (±)-Galanthamine through Phenol Oxidation" J. Chem. Soc., p. 2602–2605.
Vlahov, R. et al. (1989) "Synthesis of Galanthamine and Related Alkaloids—New Approaches. I." Tetrahedron 45(11): 3329–3345.
Szewczyk, J. et al. (1995) "Facile synthesis of (+–), (+), and (–)-galanthamine" J. Heterocyclic Chem. 32(1):195–199.

* cited by examiner

*Primary Examiner*—Bruck Kifle
(74) *Attorney, Agent, or Firm*—Saliwanchik, Lloyd & Saliwanchik

(57) ABSTRACT

The subject invention concerns a process for the preparation of a compound of formula (2), which comprises phenolic oxidation of a compound of formula (1)

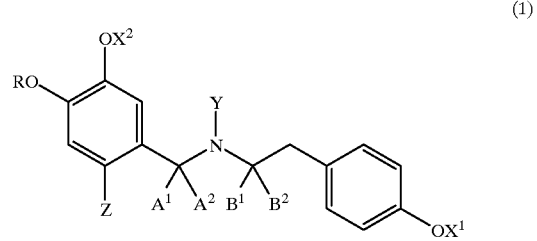

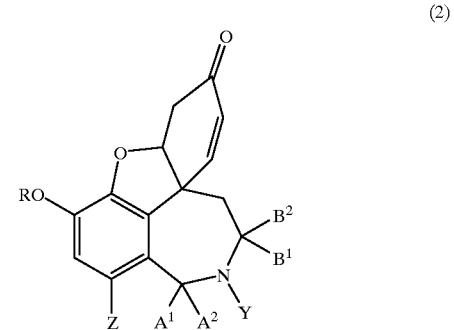

wherein $X^1$ and $X^2$ are independently selected from H or a protecting group for the phenolic function, e.g. acyl or trialkylsilyl; groups $A^1$, $A^2$, $B^1$, $B^2$ and Y are selected so as to render the nitrogen atom non-basic; Z is a blocking group, e.g. Br or t-butyl; and R is H, alkyl, aryl, or arylalkyl, and wherein the process is carried out in a two-phase liquid system comprising an aqueous base and an organic solvent having a dielectric constant below 4.8.

10 Claims, No Drawings

OXIDATIVE PROCESS AND PRODUCTS THEREOF

CROSS-REFERENCE TO RELATED APPLICATION

This application is a continuation of application Ser. No. 08/875,638 filed Jul. 16, 1997.

FIELD OF THE INVENTION

The invention relates a process for obtaining narwedine and derivatives thereof in improved yield

BACKGROUND

The phenolic oxidation of tyramine derivatives (1) to narwedine derivatives (2) is known with reagents such as potassium ferricyanide in a two phase system of chloroform and aqueous sodium hydrogen carbonate. The reaction typically gives a low yield and chromatographic purification is necessary; see for instance Szewczyk J., et al, J. Heterocyclic Chem. (1988) 25: 1809, Kametani T., et al, J. Chem. Soc (C) (1969) 2602, and Vlahov R., et al, Tetrahedron No. 11 (1989) 45: 3329.

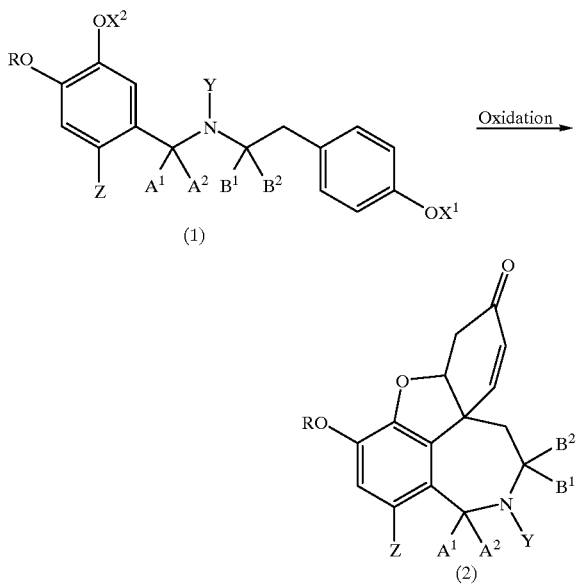

Scheme 1

SUMMARY OF THE INVENTION

According to a first aspect of the present invention a process for the preparation of a compound of formula (2) comprises phenolic oxidation of a compound of formula (1), both formulae being shown above, wherein $X^1$ and $X^2$ are independently selected from H or a protecting group for the phenolic function, eg. acyl or trialkylsilyl; groups $A^1$, $A^2$, $B^1$, $B^2$ and Y are selected so as to render the nitrogen atom non-basic; Z is a blocking group eg. Br or t-butyl; and R is H, $C_{1-20}$ alkyl, $C_{3-20}$ aryl or $C_{4-20}$ arylalkyl, and wherein the process is carried out in a two phase liquid system comprising an aqueous base and an organic solvent having a dielectric constant below 4.8.

The process of the present invention is capable of producing the target compounds (2) in higher yields than achieved by prior art processes. In addition, the products are obtained in sufficient purity in the organic phase to be recoverable by evaporation, thereby avoiding chromatographic purification and significantly improving the economics of the process.

According to a second aspect of the present invention, novel compounds having the formula (2) above are provided, wherein $X^1$ and $X^2$=H, R=Me, Z=Br and Y=COCF$_3$ or CO-t-butyl. Such compounds are readily convertible to their corresponding galanthamine structures.

DESCRIPTION OF THE INVENTION

Broadly, the phenolic oxidation reaction which embodies the present invention is represented in Scheme 1 above. The substituents $A^1$, $A^2$, $B^1$, $B^2$ and Y in the starting material (1) are selected so as to render the nitrogen atom non-basic, thereby dictating that the requisite reaction take place. By non-basic typically we mean that the starting material includes a protecting group for the N-atom, eg. a carbonyl group, optionally as part of the basic skeleton linking the two aromatic rings. Suitable examples of these substituents include $A^1=A^2=B^1=B^2=H$ and Y=COR, where R is H, $C_{1-20}$ alkyl, $C_{3-20}$ aryl, $C_{4-20}$ arylalkyl, $C_{1-20}$ alkyloxy; $A^1=A^2=O$, $B^1=B^2=Y=H$; $B^1=B^2=O$; $A^1=A^2=Y=H$, $B^1=B^2=O$; $A^1=A^2=O$, $B^1=B^2=H$ and Y=Me; and $A^1=A^2=H$, $B^1=B^2=O$ and Y=Me.

Z is a group that assists the formation of the target narwedine derivatives by blocking coupling at its position on the aromatic ring. Examples of Z include Br and $^t$Bu, but Z can be any other blocking group desired in the narwedine derivative. R is typically a methyl group so as to provide narwedine itself, but it can be other alkyl, aryl, arylalkyl, etc., for instance of upto 20 carbon atoms, or R can be H. Further substitution may also be present where a more substituted narwedine derivative is required. For instance, either or both of the aromatic rings can include further substituents, such as further halogen atoms, typically in the ring including substituent $X^1$.

The process of the invention is carried out in a two-phase liquid system comprising an aqueous base and an organic solvent having a dielectric constant less than that of chloroform, ie. less than 4.8 (as measured at 20° C.). Examples of suitable solvents include toluene, benzene, anisole, dibutyl ether, carbon tetrachloride, cyclohexane and pentane. Solvents that are particularly useful are aromatic hydrocarbons, and toluene is particularly preferred. Preferably, the reaction mixture is vigorously stirred, to ensure good mixing of components.

The process of the present invention is now illustrated by the following Examples.

EXAMPLE 1

Phenolic Oxidative Coupling of bromoformamide (general formula (1) in which $X^1=X^2$=H, R=Me, Z=Br and Y=CHO) in toluene to give bromoformylnarwedine (general formula (2) in which $X^1=X^2$=H, R=Me, Z=Br and Y=CHO)

To a solution of potassium ferricyanide (2.05 g, 6.23 mmol) in 5% NaHCO$_3$ (25 ml) was added toluene (50 ml) and bromoformamide (general formula (1) in which $X^1=X^2$=H, R=Me, Z=Br and Y=CHO) (0.440 g, 1.05 mmol) and the mixture was heated to reflux with vigorous stirring. After three hours the reaction mixture was cooled and filtered, the organic phase removed and dried over MgSO$_4$, and the solvent removed to leave bromoformylnarwedine as a clear oil (0.104 g, 26%).

COMPARATIVE EXAMPLE

Phenolic Oxidative Coupling of bromoformamide in chloroform to give bromoformylnarwedine To a well stirred mixture of chloroform (3000 ml) and 5% NaHCO₃ (400 ml) containing potassium ferricyanide (42 g, 128 mmol) at 60° C. was added bromoformamide (7.96 g, 21 mmol), and the reaction stirred at 60° C. for 20 hours.

The crude reaction material was filtered, to remove the solid waste (43 g), and the filtrate transferred to a separating funnel. The organic liquor was collected, dried over MgSO₄ and the solvent removed to leave the crude product as a brown foam (2.86 g, 36%).

Column chromatography (silica gel, 1.5% ethanol/ CH₂Cl₂) yielded the still impure coupled product (1.51 g, 19%). Further chromatography (silica gel, 2.5% ethanol/ ethyl acetate) and recrystallisation from CH₂Cl₂/ethanol yielded bromoformylnarwedine as colourless crystals (0.87 g, 11%). The product was identified by comparison of its ¹H nmr spectra with that reported in the literature (Szewczyk J., et al, J. Heterocyclic Chem., 1988, 25, 1809).

The above Example and Comparative Example confirms that when the same reaction is carried out under identical conditions except for the solvent that is used, a significantly improved yield is obtained using a solvent in accordance with the present invention ie. toluene, and isolation of the final product is much simplified, than when using chloroform as the solvent.

EXAMPLE 2

Phenolic Coupling of 2-bromo-4-methoxy-5-hydroxy-N-[2-(4-hydroxyphenyl)-ethyl]-N-methylbenzamide to give 1-bromo-10-oxo-narwedine (general formula (2) with R=Y=Me, $X^1=X^2=B^1=B^2=H$, $A^1=A^2=O$, Z=Br).

Potassium ferricyanide (1.04 g, 3.17 mmol) was dissolved in a biphasic mixture of toluene (40 ml, 100 volumes) and 5% aqueous sodium bicarbonate (20 ml, 50 volumes). The substrate, 2-bromo-4-methoxy-5-hydroxy-N-[2-(4-hydroxyphenyl)-ethyl]-N-methylbenzamide (general formula (1) with R=Y=Me, $X^1=X^2=B^1=B^2=H$, $A^1=A^2=O$, Z=Br), (0.40 g, 1.057 mmol) was added with vigorous stirring and the reaction mixture was heated to reflux (87° C.). The reaction was stirred at reflux for 3 hours before cooling to ambient temperature with gentle stirring. The mixture was filtered to give a biphasic filtrate. The toluene layer was separated from the aqueous and the volatiles removed in vacuo leaving the product as a white foam (77 mg, 0.203 mmol, 19.1%).

EXAMPLE 3

Phenolic Coupling of N-(2-bromo-4-methoxy-5-hydroxybenzyl)-N-methyl-2-(4-hydroxyphenyl)-acetamide to give 1-bromo-12-oxo-narwedine (formula (2) with R=Y=Me, $X^1=X^2=A^1=A^2=H$, $B^1=B^2=O$, Z=Br)

Potassium ferricyanide (0.51 g, 8.05 mmol) was dissolved in a biphasic mixture of toluene (50 ml, 100 volumes) and 5% aqueous sodium bicarbonate (25 ml, 50 volumes). The substrate, N-(2-bromo-4-methoxy-5-hydroxybenzyl)-N-methyl-2-(4-hydroxyphenyl)-acetamide, (general formula (1) with R=Y=Me, $X^1=X^2=A^1=A^2=H$, $B^1=B^2=O$, Z=Br), (2.65 g, 1.34 mmol) was added with vigorous stirring and the reaction mixture was heated to reflux (84° C.). The reaction was stirred at reflux for 3 hours before cooling to ambient temperature with gentle stirring. Toluene (50 ml) and 5% aqueous sodium bicarbonate (25 ml) were added and the toluene layer separated. The mixture was further extracted with toluene, and the combined toluene layers concentrated in vacuo leaving the product as a pink oil (0.10 g, 0.265 mmol, 19.8%).

What is claimed is:

1. A process for the preparation of a compound of formula (2), comprising phenolic oxidation of a compound of formula (1)

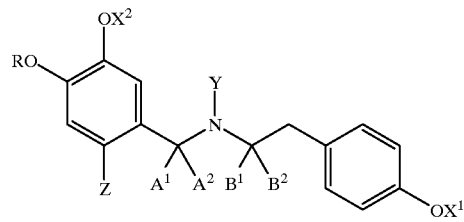

(1)

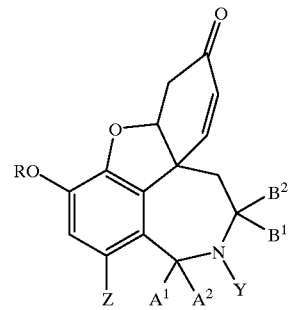

(2)

wherein $X^1$ and $X^2$ are independently selected from H or a protecting group for the phenolic function; groups $A^1$, $A^2$, $B^1$, $B^2$ and Y are selected from the group consisting of (i) wherein each of $A^1$, $A^2$, $B^1$ and $B^2$ are H and Y is $COR^1$, wherein $R^1$ is selected from the group consisting of H, alkyl, aryl, arylalkyl, and alkyloxy; (ii) wherein $A^1$ and $A^2$ are H, $B^1$ and $B^2$ are, together, O, and Y is H or Me; and (iii) wherein $A^1$ and $A^2$ are, together, O, $B^1$ and $B^2$ are H, and Y is H or Me; Z is a blocking group; and R is selected from the group consisting of H, alkyl, aryl, and arylalkyl, and wherein the process is carried out in a two phase liquid system comprising an aqueous base and an organic solvent having a dielectric constant below 4.8, as measured at 20° C., wherein said solvent is toluene.

2. The process according to claim 1, wherein $A^1$, $A^2$, $B^1$ and $B^2$=H and Y=$COR^1$, wherein $R^1$ is selected from the group consisting of H, alkyl, aryl, arylalkyl and alkyloxy.

3. The process according to claim 2, wherein $X^1$ and $X^2$=H, R=Me, Y=CHO, and Z=Br.

4. The process according to claim 1, wherein $A^1$ and $A^2$ are, together, O and $B^1=B^2=Y=H$.

5. The process according to claim 1, wherein $B^1$ and $B^2$ are, together, O and $A^1=A^2=Y=H$.

6. The process according to claim 1, wherein $A^1$ and $A^2$ are, together, O, $B^1=B^2=H$, and Y=Me.

7. The process according to claim 1, wherein $A^1=A^2=H$, $B^1$ and $B^2$ are, together, O, and Y=Me.

8. The process according to claim 1, wherein the product is recovered by evaporation without further purification.

9. The process according to claim 1, wherein the blocking group is selected from the group consisting of Br and t-butyl.

10. The process according to claim 1, wherein the protecting group for the phenolic function is selected from the group consisting of acyl and trialkylsilyl.

\* \* \* \* \*